US010135517B2

United States Patent
Yu et al.

(10) Patent No.: US 10,135,517 B2
(45) Date of Patent: Nov. 20, 2018

(54) RELAY LINK HARQ OPERATION

(71) Applicant: BlackBerry Limited, Waterloo (CA)

(72) Inventors: Yi Yu, Reston, VA (US); Zhijun Cai, Ashburn, VA (US); James Earl Womack, Bedford, TX (US); Andrew Mark Earnshaw, Kanata (CA)

(73) Assignee: BlackBerry Limited, Waterloo, Ontario (CA)

( * ) Notice: Subject to any disclaimer, the term of this patent is extended or adjusted under 35 U.S.C. 154(b) by 76 days.

(21) Appl. No.: 15/249,014

(22) Filed: Aug. 26, 2016

(65) Prior Publication Data

US 2016/0365915 A1     Dec. 15, 2016

Related U.S. Application Data

(63) Continuation of application No. 13/649,872, filed on Oct. 11, 2012, now Pat. No. 9,439,216, which is a
(Continued)

(51) Int. Cl.
*H04W 74/00*     (2009.01)
*H04W 72/14*     (2009.01)
(Continued)

(52) U.S. Cl.
CPC .............. *H04B 7/155* (2013.01); *A61K 31/00* (2013.01); *A61K 31/343* (2013.01); *A61K 45/06* (2013.01);
(Continued)

(58) Field of Classification Search
CPC ............................ H04W 72/082; H04W 72/08
(Continued)

(56) References Cited

U.S. PATENT DOCUMENTS 6,629,285 B1 * 9/2003 Gerendai .............. H04L 1/1628
714/748
7,069,038 B2    6/2006 Hakkinen et al.
(Continued)

FOREIGN PATENT DOCUMENTS

CN       101330312 A    12/2008
EP        1890440 A2    2/2008
(Continued)

OTHER PUBLICATIONS

3GPP TS 36.212 V.8.6.0; 3rd Generation Partnership Project; Technical Specification Group Radio Access Network; Evolved Universal Terrestrial Radio Access (E-UTRA); Multiplexing and Channel Coding; Release 8; Mar. 2009; 59 pages.
(Continued)

*Primary Examiner* — Iqbal Zaidi
*Assistant Examiner* — Dewanda Samuel
(74) *Attorney, Agent, or Firm* — Conley Rose, P.C.; J. Robert Brown, Jr.; Joseph J. Funston, III

(57) ABSTRACT

A method for preventing a first network node from missing a transmission from a second network node. The method includes, when a ten millisecond periodicity is used for Multicast/Broadcast Single Frequency Network (MBSFN) subframes, setting a time between an uplink grant from the second network node to the first network node and an acknowledgement/negative-acknowledgement message (ACK/NACK) from the second network node to the first network node equal to ten milliseconds. The method further includes, when a forty millisecond periodicity is used for MBSFN subframes, the second network node sending the first network node an asynchronous grant for an uplink retransmission when a data packet is missed, and when the first network node receives the grant for the uplink retrans-
(Continued)

mission, the first network node retransmitting the missed data packet.

20 Claims, 7 Drawing Sheets

Related U.S. Application Data continuation of application No. 12/429,966, filed on Apr. 24, 2009, now Pat. No. 8,289,895.

(51) Int. Cl.
```
H04W 74/08      (2009.01)
H04B 7/155      (2006.01)
H04B 7/26       (2006.01)
H04L 1/16       (2006.01)
H04L 1/18       (2006.01)
H04W 72/12      (2009.01)
A61K 45/06      (2006.01)
A61K 31/00      (2006.01)
A61K 31/343     (2006.01)
H04L 5/00       (2006.01)
H04L 12/931     (2013.01)
H04W 16/14      (2009.01)
H04L 1/00       (2006.01)
H04W 16/32      (2009.01)
```
(52) U.S. Cl.
CPC ............ *H04B 7/2606* (2013.01); *H04L 1/16* (2013.01); *H04L 1/18* (2013.01); *H04L 1/1816* (2013.01); *H04L 1/1887* (2013.01); *H04L 5/0055* (2013.01); *H04L 49/201* (2013.01); *H04W 72/1268* (2013.01); *H04W 72/1284* (2013.01); *H04W 72/14* (2013.01); *H04W 74/004* (2013.01); *H04W 74/0858* (2013.01); *H04L 2001/0097* (2013.01); *H04W 16/32* (2013.01); *H04W 72/1294* (2013.01)

(58) Field of Classification Search
USPC .................................................. 370/328–339
See application file for complete search history.

(56) References Cited

U.S. PATENT DOCUMENTS

| | | | |
|---|---|---|---|
| 7,774,686 B2 | 8/2010 | Ahn et al. | |
| 7,792,026 B2 * | 9/2010 | Wang | H04L 1/1841 370/229 |
| 8,140,928 B2 | 3/2012 | Umesh et al. | |
| 8,289,895 B2 | 10/2012 | Yu et al. | |
| 8,402,335 B2 | 3/2013 | Doppler et al. | |
| 8,634,343 B2 | 1/2014 | Hart et al. | |
| 8,671,322 B2 | 3/2014 | Wong | |
| 8,804,650 B2 | 8/2014 | Horiuchi et al. | |
| 8,971,241 B2 * | 3/2015 | Palanki | H04B 7/2606 370/328 |
| 9,439,216 B2 | 9/2016 | Yu et al. | |
| 2002/0124096 A1 * | 9/2002 | Loguinov | H04L 1/0001 709/230 |
| 2006/0083233 A1 | 4/2006 | Nishibayashi et al. | |
| 2006/0153154 A1 | 7/2006 | Yoon et al. | |
| 2006/0195753 A1 | 8/2006 | Nam et al. | |
| 2007/0030839 A1 | 2/2007 | Vimpari et al. | |
| 2008/0068979 A1 * | 3/2008 | Visotsky | H04L 1/1825 370/208 |
| 2008/0225776 A1 * | 9/2008 | Alanara | H04L 1/189 370/315 |
| 2008/0279145 A1 | 11/2008 | Boariu et al. | |
| 2009/0046649 A1 * | 2/2009 | Gao | H04L 1/1861 370/329 |
| 2009/0213769 A1 | 8/2009 | Shen et al. | |
| 2009/0221231 A1 | 9/2009 | Weng et al. | |
| 2009/0313518 A1 | 12/2009 | Shen et al. | |
| 2010/0080139 A1 | 4/2010 | Palanki et al. | |
| 2010/0110964 A1 | 5/2010 | Love et al. | |
| 2010/0238870 A1 | 9/2010 | Mitra et al. | |
| 2011/0200016 A1 | 8/2011 | Bergman et al. | |

FOREIGN PATENT DOCUMENTS

| | | |
|---|---|---|
| EP | 2400673 A2 | 12/2011 |
| KR | 20080089118 A | 10/2008 |
| WO | 2008120932 A1 | 10/2008 |
| WO | 2008120958 A1 | 10/2008 |
| WO | 2009020876 A1 | 2/2009 |
| WO | 2009031866 A2 | 3/2009 |
| WO | 2010038315 A1 | 4/2010 |
| WO | 2010057521 A1 | 5/2010 |
| WO | 2010073630 A1 | 7/2010 |

OTHER PUBLICATIONS

3GPP TR 36.814 V0.4.1; 3rd Generation Partnership Project; Technical Specification Group Radio Access Network; Further Advancements for E-UTRA Physical Layer Aspects; Release 9; Feb. 2009; 31 pages.
Huawei, 3GPP TSG RAN WG1 Meeting #56bis; "Relay Frame Structure Design of TDD Mode"; R1-091270; Seoul, Korea; Mar. 23-27, 2009; 10 pages.
Research in Motion UK Limited, 3GPP TSG RAN WG1 Meeting #59bis; "Relay Link HARQ Operation"; R1-100572; Valencia, Spain; Jan. 18-22, 2010; 8 pages.
Texas Instruments, 3GPP TSG RAN WG1 #56; "On the Design of Relay Node for LTE-Advanced"; R1-090593; Athens, Greece; Feb. 9-13, 2009; 11 pages.
Panasonic, 3GPP TSG RAN WG2 #67bis; "UL HARQ Protocol for Un Interface; R2-095607"; Miyazaki, Japan; Oct. 12-16, 2009; 4 pages.
Research in Motion UK Limited, 3GPP TSG RAN WG1 Meeting #67; "UL HARQ Operation over Un Interface"; R2-094286; Shenzhen, China, Aug. 24-28, 2009; 3 pages.
Ericsson; TSG-RAN WG1 #55; "Efficient Support of Relays Through MBSFN Subframes"; R1-084357; Prague, Czech Republic; Nov. 10-14, 2008; 3 pages.
Qualcomm Europe; 3GPP TSG RAN WG1 #55 Meeting; "Comparing Relay Support with MBSFN and Blank Subframes"; R1-084515; Prague, Czech Republic; Nov. 10-14, 2008; 4 pages.
TSG-RAN WG1 #56; "Uplink Asynchronous HARQ for Relay Link;" R1-090642; Athens, Greece; Feb. 9-13, 2009; 3 pages.
3GPP TSG-RA WG1 #56; "Preference for Relay Operation in LTE-A;" R1-091049; Athens, Greece; Feb. 9-13, 2009; 9 pages.
3GPP TSG-RAN WG2 Meeting #67bis; "UL HARQ Operation Over Un Interface;" R2-095833; Miyazaki, Japan; Oct. 12-16, 2009; 3 pages.
3GPP TSG RAN WG1 Meeting #56; "Summary and Proposal of Relay Frame Structure"; R1-090827; Athens, Greece; Feb. 9-13, 2009; 6 pages.
Office Action dated Jan. 30, 2012; U.S. Appl. No. 12/429,966, filed Apr. 24, 2009; 28 pages.
Notice of Allowance dated Jun. 15, 2012; U.S. Appl. No. 12/429,966, filed Apr. 24, 2009; 10 pages.
Office Action dated Nov. 20, 2014; U.S. Appl. No. 13/649,872, filed Oct. 11, 2012; 45 pages.
Office Action dated May 21, 2015; U.S. Appl. No. 13/649,872, filed Oct. 11, 2012; 16 pages.
Office Action dated Jan. 5, 2016; U.S. Appl. No. 13/649,872, filed Oct. 11, 2012; 12 pages.
Notice of Allowance dated May 4, 2016; U.S. Appl. No. 13/649,872, filed Oct. 11, 2012; 10 pages.
PCT International Search Report; PCT Application No. PCT/US2010/031767; dated Nov. 17, 2010; 3 pages.

(56) References Cited

OTHER PUBLICATIONS

PCT Written Opinion of the International Searching Authority; PCT Application No. PCT/US2010/031767; dated Nov. 17, 2010; 5 pages.
Extended European Search Report; Application No. 10161011.1; dated Jan. 20, 2011; 7 pages.
European Intent to Grant; Application No. 10161011.1; dated Oct. 10, 2011; 6 pages.
Extended European Search Report; Application No. 10161012.9; dated Sep. 23, 2010; 8 pages.
European Examination Report; Application No. 10161012.9; dated Sep. 6, 2011; 8 pages.
European Summons to Attend Oral Proceedings; Application No. 10161012.9; Jun. 7, 2013; 7 pages.
Extended European Search Report; Application No. 10161014.5; dated Sep. 8, 2010; 6 pages.
European Examination Report; Application No. 10161014.5; dated May 22, 2012; 4 pages.
Extended European Search Report; Application No. 11181123.8; dated Oct. 7, 2011; 7 pages.
Canadian Office Action; Application No. 2,759,910; dated Aug. 21, 2013; 2 pages.
Chinese Office Action; Application No. 201080028226.2; dated Nov. 18, 2013; 10 pages.
Japanese Office Action; Application No. 2012-507323; dated Jan. 11, 2013; 9 pages.
Korean Office Action; Application No. 10-2011-7028103; dated Sep. 26, 2012; 6 pages.
Extended European Search Report; Application No. 12160351.8; dated May 31, 2012; 7 pages.

\* cited by examiner

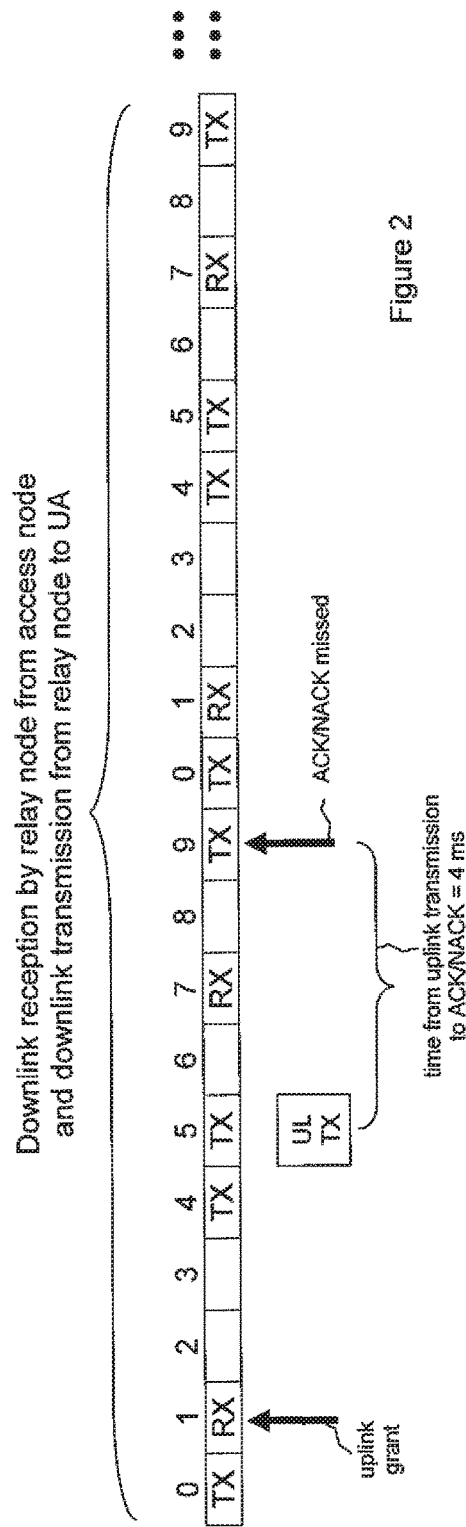
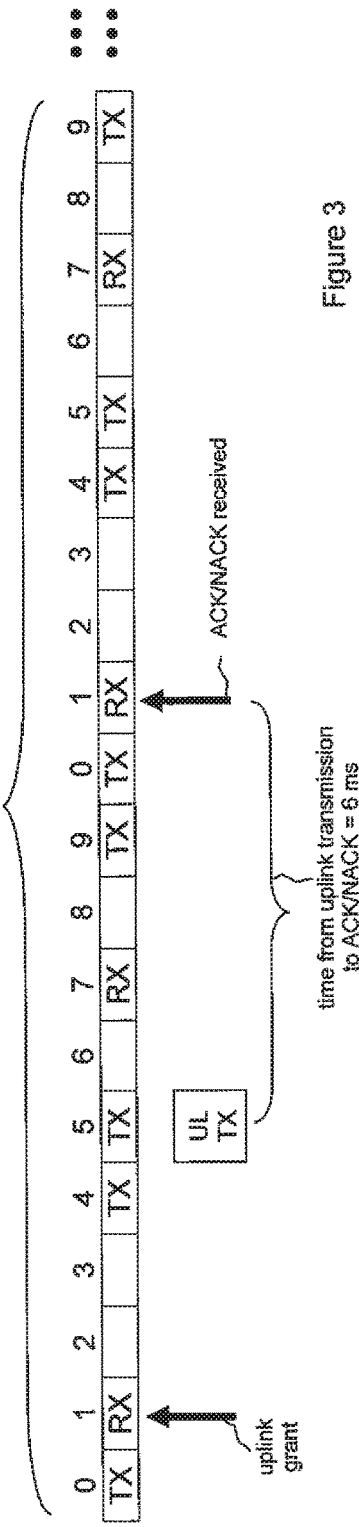

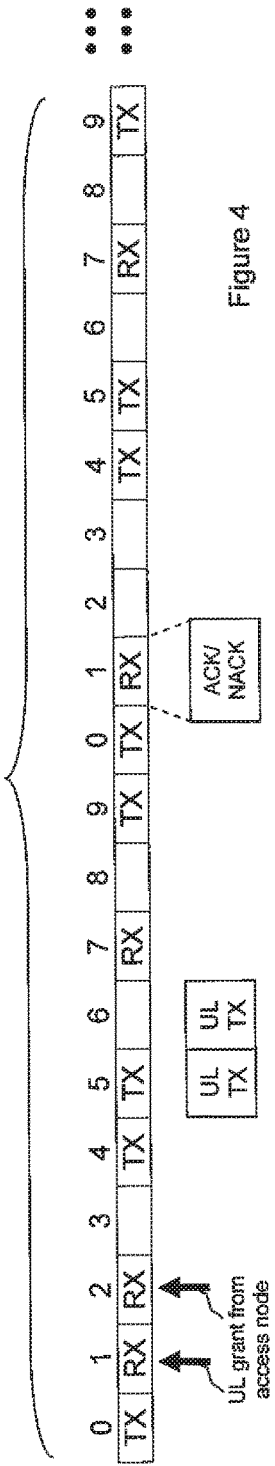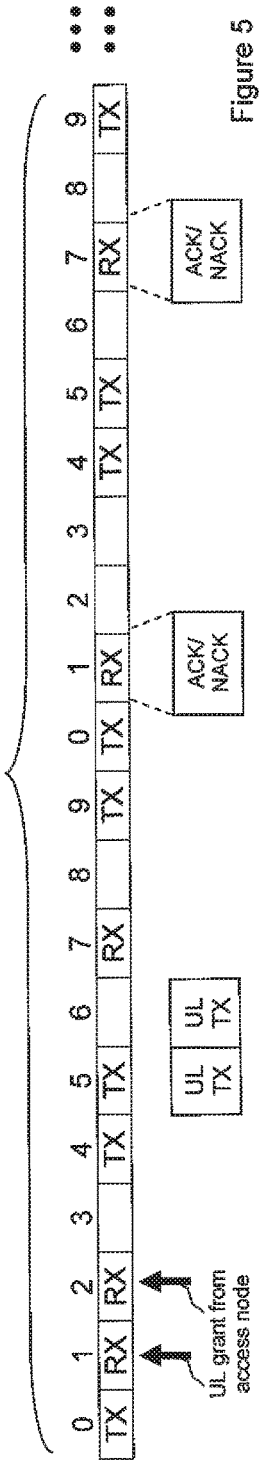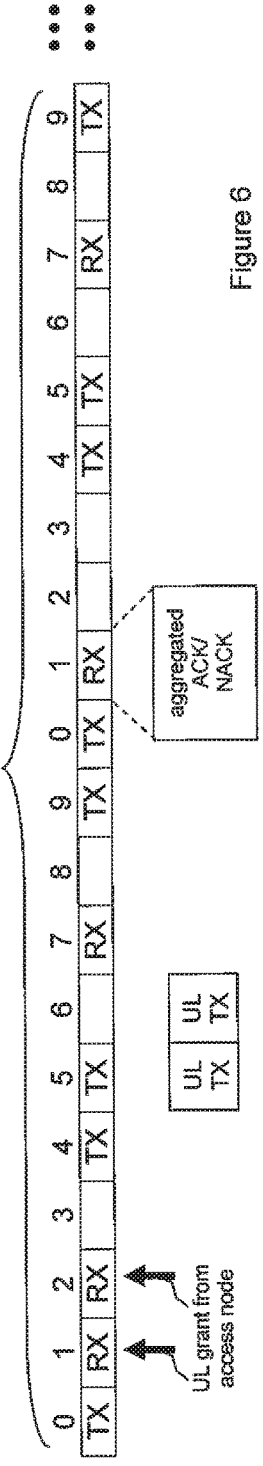

| MBSFN Subframe | Corresponding ACK/NACK Subframe |
|---|---|
| 2 | 13 |
| 13 | 22 |
| 22 | 33 |
| 33 | 2 |

Figure 7

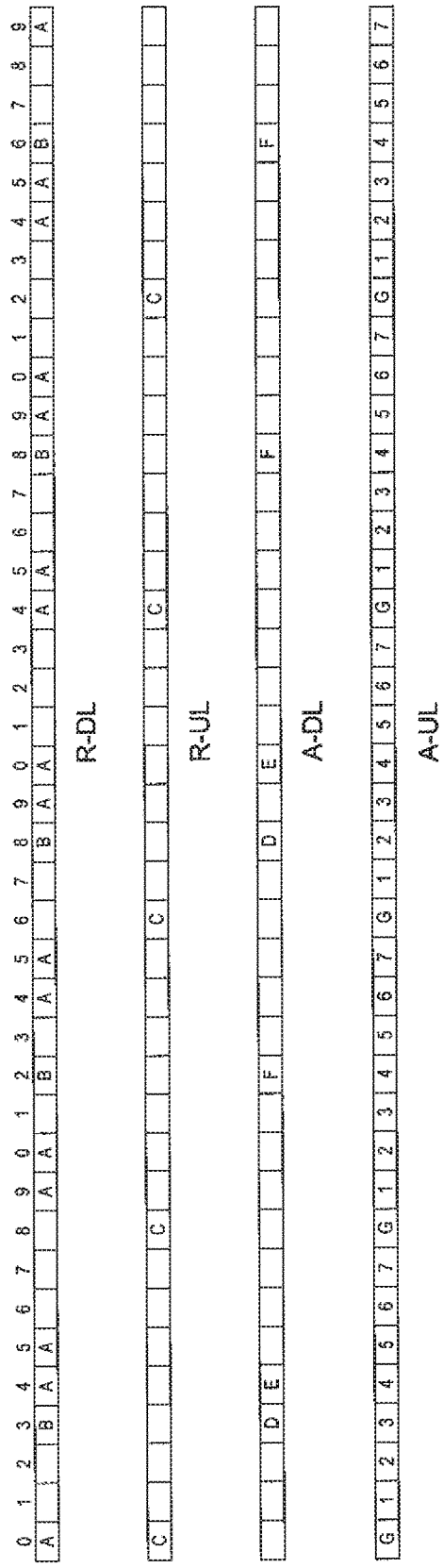
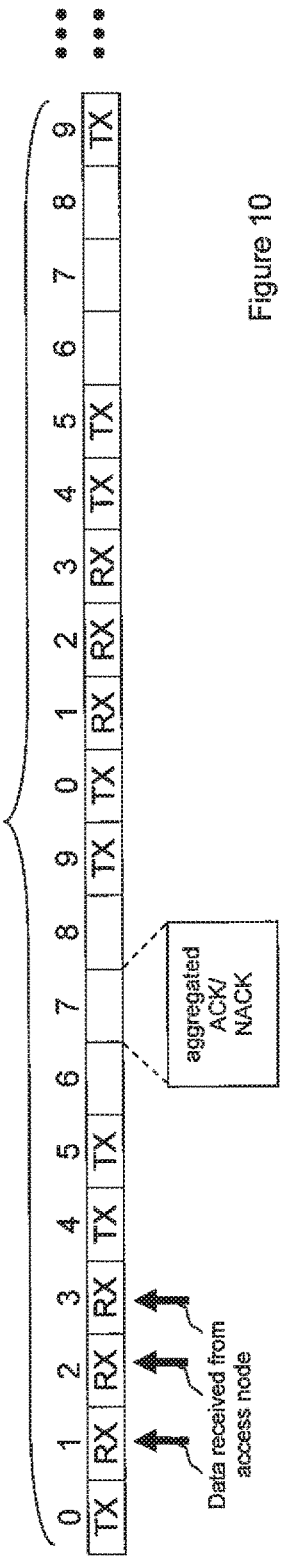
Figure 9
Figure 10

RELAY LINK HARQ OPERATION

CROSS-REFERENCE TO RELATED APPLICATIONS

This application is a continuation of U.S. patent application Ser. No. 13/649,872 filed Oct. 11, 2012 by Yi Yu, et al. entitled, "Relay Link HARQ Operation", which is a continuation of U.S. Pat. No. 8,289,895 issued on Oct. 16, 2012 entitled, "Relay Link HARQ Operation", both of which are incorporated by reference herein as if reproduced in their entirety.

BACKGROUND

As used herein, the terms "user agent" and "UA" might in some cases refer to mobile devices such as mobile telephones, personal digital assistants, handheld or laptop computers, and similar devices that have telecommunications capabilities. Such a UA might consist of a device and its associated removable memory module, such as but not limited to a Universal Integrated Circuit Card (UICC) that includes a Subscriber Identity Module (SIM) application, a Universal Subscriber Identity Module (USIM) application, or a Removable User Identity Module (R-UIM) application. Alternatively, such a UA might consist of the device itself without such a module. In other cases, the term "UA" might refer to devices that have similar capabilities but that are not transportable, such as desktop computers, set-top boxes, or network appliances. The term "UA" can also refer to any hardware or software component that can terminate a communication session for a user. Also, the terms "user agent," "UA," "user equipment," "UE," "user device" and "user node" might be used synonymously herein.

As telecommunications technology has evolved, more advanced network access equipment has been introduced that can provide services that were not possible previously. This network access equipment might include systems and devices that are improvements of the equivalent equipment in a traditional wireless telecommunications system. Such advanced or next generation equipment may be included in evolving wireless communications standards, such as long-term evolution (LTE). For example, an LTE system might include an Evolved Universal Terrestrial Radio Access Network (E-UTRAN) node B (eNB), a wireless access point, or a similar component rather than a traditional base station. As used herein, the term "access node" will refer to any component of a wireless telecommunications system, such as a traditional base station, a wireless access point, or an LTE eNB, that creates a geographical area of reception and transmission coverage allowing a UA or a relay node to access other components in the system. An access node may comprise a plurality of hardware and software.

The term "access node" does not refer to a relay node, which is a component in a wireless network that is configured to extend or enhance the coverage created by an access node or another relay node. The access node and relay node are both radio components that may be present in a wireless communications network, and the terms "component" and "network node" may refer to an access node or relay node. It is understood that a component might operate as an access node or a relay node depending on its configuration and placement. However, a component is called a "relay node" only if it requires the wireless coverage of an access node or other relay node to access other components in a wireless communications system. Additionally, two or more relay nodes may be used serially to extend or enhance coverage created by an access node.

The signals that carry data between UAs, relay nodes, and access nodes can have frequency, time, and coding parameters and other characteristics that might be specified by a network node. A connection between any of these elements that has a specific set of such characteristics can be referred to as a resource. The terms "resource," "communications connection," "channel," and "communications link" might be used synonymously herein. A network node typically establishes a different resource for each UA or other network node with which it is communicating at any particular time.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

FIG. 2 is a diagram of a timeline for downlink transmissions to and from a relay node.

FIG. 3 is a diagram of a timeline for downlink transmissions to and from a relay node according an embodiment of the disclosure.

FIG. 4 is an alternative diagram of a timeline for downlink transmissions to and from a relay node.

FIG. 5 is a diagram of a timeline for downlink transmissions to and from a relay node according an alternative embodiment of the disclosure.

FIG. 6 is a diagram of a timeline for downlink transmissions to and from a relay node according an alternative embodiment of the disclosure.

FIG. 7 is a diagram of a mapping of MBSFN subframes and corresponding ACK/NACK subframes according an embodiment of the disclosure.

FIG. 9 is a diagram of multiple timelines depicting a technique for avoiding collisions between uplink transmission from a relay node and uplink transmissions from a UA according to an embodiment of the disclosure.

FIG. 10 is a diagram of a timeline for downlink transmissions to and from a relay node according an alternative embodiment of the disclosure.

DETAILED DESCRIPTION

It should be understood at the outset that although illustrative implementations of one or more embodiments of the present disclosure are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Figure 1:
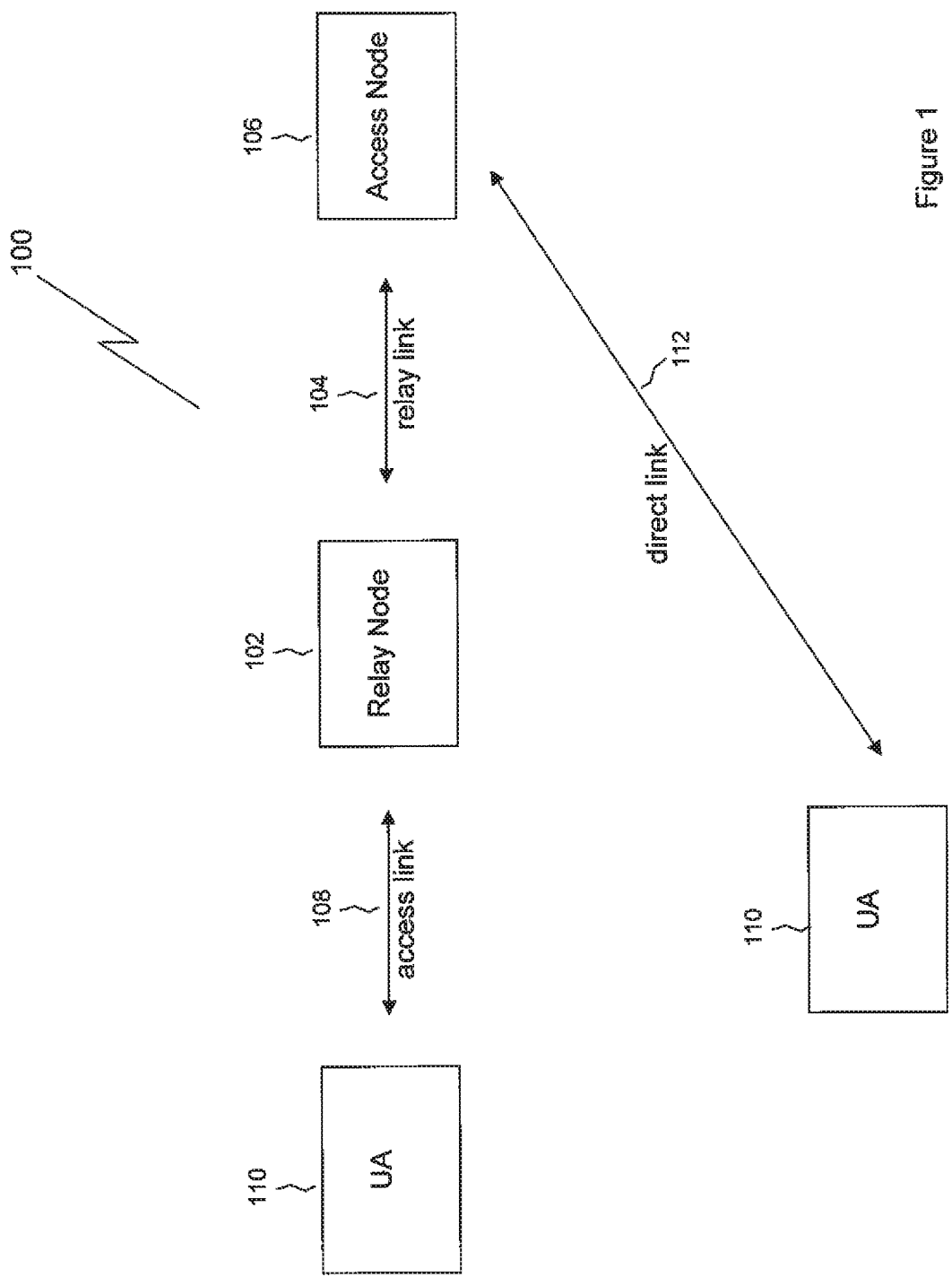
FIG. 1 is a diagram illustrating a wireless communication system that includes a relay node, according to an embodiment of the disclosure.

FIG. 1 is a diagram illustrating a wireless communication system 100 that includes a relay node 102, according to an embodiment of the disclosure. Examples of the wireless communication system 100 include LTE or LTE-Advanced (LTE-A) networks, and all of the disclosed and claimed embodiments could be implemented in an LTE-A network. The relay node 102 can amplify or repeat a signal received from a UA 110 and cause the modified signal to be received at an access node 106. In some implementations of a relay node 102, the relay node 102 receives a signal with data from the UA 110 and then generates a new signal to transmit the data to the access node 106. The relay node 102 can also receive data from the access node 106 and deliver the data to the UA 110.

The relay node 102 might be placed near the edges of a cell so that the UA 110 can communicate with the relay node 102 rather than communicating directly with the access node 106 for that cell. In radio systems, a cell is a geographical area of reception and transmission coverage. Cells can overlap with each other. In the typical example, there is one access node associated with each cell. The size of a cell is determined by factors such as frequency band, power level, and channel conditions. Relay nodes, such as relay node 102, can be used to enhance coverage within a cell or to extend the size of coverage of a cell. Additionally, the use of a relay node 102 can enhance throughput of a signal within a cell because the UA 110 can access the relay node 102 at a higher data rate than the UA 110 might use when communicating directly with the access node 106 for that cell, thus creating higher spectrum efficiency. The use of a relay node 102 can also decrease the UA's battery usage by allowing the UA 110 to transmit at a lower power.

Relay nodes can be divided into three types: layer one relay nodes, layer two relay nodes, and layer three relay nodes. A layer one relay node is essentially a repeater that can retransmit a transmission without any modification other than amplification and slight delay. A layer two relay node can decode a transmission that it receives, re-encode the result of the decoding, and then transmit the re-encoded data. A layer three relay node can have full radio resource control capabilities and can thus function similarly to an access node. The radio resource control protocols used by a relay node may be the same as those used by an access node, and the relay node may have a unique cell identity typically used by an access node. The illustrative embodiments are primarily concerned with layer two or layer three relay nodes. Therefore, as used herein, the term "relay node" will not refer to layer one relay nodes, unless specifically stated otherwise.

When the UA 110 is communicating with the access node 106 via the relay node 102, the links that allow wireless communication can be said to be of three distinct types. The communication link between the UA 110 and the relay node 102 is said to occur over an access link 108. The communication between the relay node 102 and the access node 106 is said to occur over a relay link 104. Communication that passes directly between the UA 110 and the access node 106 without passing through the relay node 102 is said to occur over a direct link 112.

Data is transmitted between the access node 106, the relay node 102, and the UA 110 in a series of subframes, each typically having a duration of 1 millisecond (ms). Ten contiguous subframes comprise one radio frame. Each subframe consists of a relatively shorter control region followed by a relatively longer data region. The control region, or physical downlink control channel (PDCCH), typically consists of one to four orthogonal frequency-division multiplexing (OFDM) symbols. The data region, or physical downlink shared channel (PDSCH), can be considerably longer.

Some subframes contain unicast control data in the PDCCH region and multicast/broadcast data in the PDSCH region in order to support the Multimedia Broadcast/Multicast service (MBMS). For historical reasons, such subframes are known as Multicast/Broadcast Single Frequency Network (MBSFN) subframes. In a unicast system, if a subframe is configured as an MBSFN subframe, the subframe contains data only in the PDCCH region and there is no data in the PDSCH region. In a non-MBSFN subframe, data is typically transmitted throughout the duration of the subframe. In an MBSFN subframe, the relay node 102 transmits downlink data only for the duration of the PDCCH region. The relay node 102 then disables its downlink transmitter and enables its downlink receiver for the remainder of the subframe. For various technical and expense reasons, the relay node 102 typically cannot transmit and receive data within the same frequency band at the same time. Therefore, the relay node 102 can typically receive data from the access node 106 in an MBSFN subframe only after the relay node 102 has completed transmitting PDCCH data, disabled its downlink transmitter, and enabled its downlink receiver.

MBSFN subframes can occur in subframes 1, 2, 3, 6, 7, or 8 of a radio frame (with indexing beginning at 0), but will not necessarily occur in all of those subframes. The access node 106 specifies which subframes will be MBSFN subframes and signals that information to the relay nodes and the UAs. This could be done via higher layer control signaling. The access node 106 transmits data to the relay node 102 only in MBSFN subframes, so from the perspective of the relay node 102, MBSFN subframes can be considered reception subframes. Downlink transmissions from the relay node 102 to the UA 110 must occur in subframes 0, 4, 5, and 9 of a radio frame, and may occur in the remaining subframes. Therefore, from the perspective of the relay node 102, subframes 0, 4, 5, and 9 can be considered mandatory transmission subframes.

Among the data that the relay node 102 might receive from the access node 106 in an MBSFN subframe is an uplink grant informing the relay node 102 of a resource that the relay node 102 can use to transmit data to the access node 106. When the relay node 102 wishes to send data to the access node 106, the relay node 102 can send a resource request to the access node 106. The access node 106 can then, in a downlink transmission to the relay node 102, allocate a resource to the relay node 102 that the relay node 102 can use to send its data to the access node 106. That is, in an MBSFN subframe, the access node 106 might grant the relay node 102 the use of a communication channel with a specific set of frequency parameters and other characteristics that the relay node 102 can use on an uplink to the access node 106. In a similar way, the relay node 102 can grant an uplink resource to the UA 110 that the UA 110 can use to send data to the relay node 102.

Hybrid Automatic Repeat Request (HARQ) is an error control method that might be used in data transmissions between the access node 106, the relay node 102, and the UA 110. In HARQ, additional error detection and correction bits are added to a data transmission. If the recipient of the transmission is able to successfully decode the transmitted bits, then the recipient accepts the data block associated with the encoded bits. If the recipient is not able to decode the transmitted bits, the recipient might request a retransmission. For example, upon receiving a downlink transmission from the access node 106, the relay node 102 would attempt to decode the error detection bits. If the decoding is successful, the relay node 102 accepts the data packet associated with the data transmission and sends an acknowledgement (ACK) message to the access node 106. If the decoding is unsuccessful, the relay node 102 places the data packet associated with the data transmission in a buffer and sends a negative-acknowledgement (NACK) message to the access node 106. Hereinafter, an ACK message or a NACK message will be referred to as an ACK/NACK.

When the access node 106 gives an uplink grant to the relay node 102 or when the relay node 102 gives an uplink grant to the UA 110, the component receiving the grant typically transmits on the uplink 4 ms later. The component that is transmitted to (i.e., the component that provided the grant) typically returns an ACK/NACK to the transmitting component 4 ms after the transmission. Therefore, the typical round trip time from the uplink grant to the ACK/NACK is 8 ms.

MBSFN subframes can have a periodicity of either 10 ms or 40 ms, depending on how often a pattern of MBSFN subframes is repeated. When the same subframes in every radio frame are MBSFN subframes, the periodicity is 10 ms. For example, if subframes 1 and 7 in every radio frame of a series of radio frames were MBSFN subframes, the MBSFN periodicity would be 10 ms. Alternatively, the pattern of MBSFN subframes within a series of radio frames might be repeated every 40 ms. For example, subframes 1 and 7 in a first radio frame might be MBSFN subframes, subframes 2 and 8 in a second radio frame might be MBSFN subframes, subframe 3 in a third radio frame might be an MBSFN subframe, and subframe 6 in a fourth radio frame might be an MBSFN subframe. This pattern of MBSFN subframes might then be repeated starting with a fifth radio frame. In such a case, the MBSFN subframe periodicity would be 40 ms.

The relay node 102 can transmit reference signals, ACK/NACKs, and uplink grants to the UA 110 in the first few symbols of what would otherwise be a reception subframe for the relay node 102. After transmitting such information, the relay node 102 switches to a receive mode to receive data from the access node 106.

Several HARQ-related issues might arise involving conflicts among the transmissions that occur in the access link 108 and the relay link 104. Some issues might be related to the relay node 102 missing a transmission from the access node 106, other issues might be related to the relay node 102 missing a transmission from the UA 110, and other issues might be related to the transmission of multiple ACK/NACKS.

If a relay node happens to be scheduled to transmit to a UA on the downlink 8 ms after the relay node receives an uplink grant from an access node, interference will occur between the relay node's transmission to the UA and the relay node's reception of an ACK/NACK from the access node. More specifically, 4 ms after receiving an uplink grant, the relay node transmits on the uplink to the access node. 4 ms after the uplink transmission, the access node sends an ACK/NACK to the relay node. If the relay node was already scheduled for transmission to the UA on the downlink at that time (for example, in subframes 0, 4, 5, 9), the relay node would need to receive the ACK/NACK on the downlink from the access node and transmit on the downlink to the UA at the same time. Since the relay node cannot receive and transmit on the same frequency band at the same time, the relay node would not receive the ACK/NACK from the access node.

This problem is illustrated in FIG. 2, where a timeline of downlink receptions by a relay node from an access node and downlink transmissions from the relay node to a UA is depicted. In this example, subframes 1 and 7 are MBSFN subframes. That is, the relay node can receive data on a downlink from the access node in subframes 1 and 7. The capability to receive on the downlink in a subframe is denoted by the letters "RX" in that subframe. In other examples, other subframes could be MBSFN subframes. Also, an MBSFN periodicity of 10 ms is shown in this example. That is, subframes 1 and 7 are MBSFN subframes in every radio frame. Downlink transmissions from the relay node to the UA must occur at subframes 0, 4, 5, and 9, as described above. The requirement to transmit a full subframe on the downlink in a subframe is denoted by the letters "TX" in that subframe. Other subframes could be also used for the downlink transmissions from the relay node to the UA.

In this example, the relay node receives an uplink grant from the access node at subframe 1. 4 ms later, at subframe 5, the relay node transmits on the uplink to the access node. (Only a portion of the timeline for uplink transmissions to and from the relay node is shown in the figure.) 4 ms after the relay node transmits to the access node, the access node sends an ACK/NACK to the relay node. That is, the access node sends the ACK/NACK at subframe 9. However, a downlink transmission from the relay node to the UA was already scheduled to occur at subframe 9 (i.e., the MBSFN subframe configuration cannot be in subframe 0, 4, 5, 9 in a radio frame). The relay node cannot receive the ACK/NACK and transmit to the UA at the same time, so the relay node misses the ACK/NACK that the access node sends at subframe 9.

In an embodiment, a multi-mode HARQ transmission scheme can be used to solve the problem of the relay node missing an ACK/NACK from the access node. That is, the solution includes two parts, one addressing cases where the MBSFN subframe periodicity is 10 ms, and one addressing cases where the MBSFN subframe periodicity is 40 ms.

When the MBSFN subframe periodicity is 10 ms, synchronous retransmission is used. In synchronous retransmission, a component retransmits a data packet at a specified time after receiving a NACK from another component to which it transmitted the data packet. In an embodiment, the timing of HARQ transmissions from the access node to the relay node is modified such that the access node sends the relay node an ACK/NACK 6 ms after an uplink transmission from the relay node to the access node, rather than the standard 4 ms later, while the relay node always transmits the data to the access node 4 ms after the uplink grant is received. In another embodiment, the relay node receives the uplink grant in subframe k, and the relay node transmits the data to the access node in subframe k+m while the access node sends the relay node an ACK/NACK in subframe k+10 (here m is less than 10). In this way, the round trip time from the time of the uplink grant to the time of the ACK/NACK is then 10 ms. Changing the timing of the ACK/NACK in this manner ensures that, when the periodicity is 10 ms, the access node never sends an ACK/NACK when the relay node is trying to transmit on the downlink. The ACK/NACK is always sent 10 ms after the relay node receives an uplink grant, and receiving an uplink grant always occurs in an MBSFN subframe. Since the periodicity is 10 ms, the subframe that occurs 10 ms after an uplink grant will also be an MBSFN subframe, and the ACK/NACK can be received in that MBSFN subframe.

An example of this partial solution is illustrated in FIG. 3, which shows a relay node downlink timeline with the same MBSFN subframe pattern and periodicity as that in FIG. 2.

The relay node again receives an uplink grant from the access node at subframe 1 and transmits on the uplink 4 ms later, at subframe 5. (Again, only a portion of the timeline for relay node uplink transmissions is shown.) In this embodiment, the access node sends an ACK/NACK to the relay node 6 ms after the relay node transmits on the uplink to the access node. That is, since the round trip time is now 10 ms, the access node sends the relay node an ACK/NACK 10 ms after providing the uplink grant. This places the ACK/NACK at subframe 1 of the next radio frame. Since subframe 1 of the second radio frame, like subframe 1 of the first radio frame, is an MBSFN subframe, the relay node can receive the ACK/NACK.

This partial solution may not be appropriate when the periodicity is 40 ms. In that case, each radio frame in a set of four consecutive radio frames might have a different pattern of MBSFN subframes. If the ACK/NACK from the access node to the relay node is set to always occur in the same subframe of each radio frame, the ACK/NACK might occur in a "receive" subframe in one radio frame, but that subframe might be a "transmit" subframe in one or more of the other three radio frames of that set of four. Therefore, the interference problems described above could occur.

For example, subframe 1 might be an MBSFN subframe in the first of four consecutive radio frames, and the relay node might receive an uplink grant in that subframe. If the round trip time is set to 10 ms, as described above, the access node would send the relay node an ACK/NACK at subframe 1 of the next radio frame. However, the next radio frame might have a different MBSFN subframe pattern, and subframe 1 of that radio frame might be a subframe in which the relay is scheduled to transmit on the downlink. The relay node would not be able to receive the ACK/NACK and transmit on the downlink at the same time, and the ACK/NACK would be missed.

Therefore, in an embodiment, when the MBSFN subframe periodicity is 40 ms, asynchronous retransmission is used. In asynchronous retransmission, a component may be instructed to retransmit a data packet at an arbitrary (rather than fixed) time after the original data packet transmission. More specifically, in this portion of the solution in this embodiment, the access node does not send an ACK/NACK to the relay node. Instead, the access node sends the relay node a grant for an uplink retransmission when retransmission is required and does not send a grant when retransmission is not required. When the relay node receives the grant for the uplink retransmission, the relay node regards the grant as a request for a retransmission, and it retransmits the missed data packet in the corresponding scheduled uplink "transmit" subframe. The problem of the relay node missing an ACK/NACK is eliminated because the access node never sends an ACK/NACK in this case.

A complete solution in this embodiment is therefore to use a multi-mode HARQ transmission, with a different mode for each of the two possible MBSFN periodicities. When the MBSFN periodicity is 10 ms, synchronous retransmission and a 10 ms round trip time are used. When the MBSFN periodicity is 40 ms, asynchronous retransmission is used, and the access node informs the relay node of the need for a retransmission by sending an uplink grant rather than a NACK. In another embodiment, asynchronous retransmission applies for MBSFN periodicities of both 10 ms and 40 ms. That is, regardless of whether a 10 ms periodicity or a 40 ms periodicity is used, the access node sends the relay node an asynchronous grant for an uplink retransmission when a data packet is missed, and when the relay node receives the grant for the uplink retransmission, the relay node retransmits the missed data packet.

In an alternative embodiment, the problem of the relay node missing an ACK/NACK from the access node after sending an uplink transmission to the access node is addressed in a different manner. In this case, the access node does not send an ACK/NACK 4 ms after receiving an uplink transmission from the relay node, as might be done under current procedures. Instead, the access node sends an ACK/NACK to the relay node in the first MBSFN subframe that is at least 4 ms after the uplink transmission from the relay node.

For example, if subframes 1 and 7 in a radio frame are MBSFN subframes, and the access node sends the relay node an uplink grant at subframe 1, the relay node will transmit on the uplink to the access node 4 ms later, at subframe 5. The access node will then send an ACK/NACK to the relay node at the next MBSFN subframe that is more than 4 ms later, which would be subframe 1 in the next radio frame. Since the ACK/NACKs are always transmitted in MBSFN subframes, there will be no conflict caused by the relay node attempting to receive an ACK/NACK in a subframe in which the relay node is scheduled to transmit.

It is possible that the relay node could send multiple uplink transmissions to the access node before the next opportunity for the access node to transmit an ACK/NACK to the relay node. The access node would need to send an ACK/NACK for each of the uplink transmissions but may not necessarily be able to send the ACK/NACKs in the same subframe. FIG. 4 illustrates an example where subframes 1 and 2 are MBSFN subframes in which uplink grants are provided to the relay node. Uplink transmissions from the relay to the access node then occur 4 ms later at subframes 5 and 6. The next MBSFN subframe that is at least 4 ms later than the uplink transmissions is at subframe 1 of the next radio frame, so the ACK/NACKs for the uplink transmissions that occurred at subframes 5 and 6 might, under a preliminary solution, occur at subframe 1. Under current procedures, however, two ACK/NACKs cannot occur in the same subframe.

Such a situation might be addressed in one of two different ways. In one embodiment, the ACK/NACK for the second uplink transmission can be delayed to the next MBSFN subframe that does not already have a scheduled ACK/NACK. This is illustrated in FIG. 5, where the ACK/NACK for the uplink transmission that occurred at subframe 5 occurs at subframe 1 of the next radio frame, and the ACK/NACK for the uplink transmission that occurred at subframe 6 occurs at subframe 7 of the next radio frame. This embodiment could add delays in the return of the ACK/NACKS, but no modifications would be needed to the current procedures for ACK/NACK coding.

In an alternative embodiment, multiple ACK/NACKs could be aggregated into a single ACK/NACK transmission. This is illustrated in FIG. 6, where both of the ACK/NACKs for the uplink transmissions that occurred at subframes 5 and 6 are aggregated into a single ACK/NACK transmission that occurs in subframe 1. This embodiment avoids delays in the return of the ACK/NACKS but may require changes to the current procedures for ACK/NACK coding.

The problem of the relay node missing an ACK/NACK from the access node after sending an uplink transmission to the access node is addressed in yet another manner in another alternative embodiment. In this case, for every MBSFN subframe in which the access node grants an uplink resource to the relay node, a corresponding MBSFN subframe is assigned in which the relay node can receive an ACK/NACK from the access node for the uplink transmission that the relay node sent to the access node on the granted resource. The mapping between the uplink grant MBSFN subframes and the ACK/NACK subframes can be explicitly signaled from the access node to the relay node during MBSFN configuration, or implicitly defined by certain rules.

FIG. 7 illustrates an example of such a mapping between MBSFN subframes. In this example, MBSFN subframe 2 is designated as a subframe in which an uplink grant will occur, and subframe 13 is designated as the subframe in which an ACK/NACK will be returned for the transmission on the uplink that was granted in subframe 2. Similarly, subframes 13, 22, and 33 are designated as uplink grant subframes, and subframes 22, 33, and 2, respectively, are designated as the corresponding ACK/NACK subframes. In other examples, other mappings between MBSFN subframes and corresponding ACK/NACK subframes could be used. The mapping can be semi-static, and the signaling that is used to send the mapping from the access node to the relay node can be higher layer signaling such as radio resource control (RRC) signaling or media access control (MAC) control elements.

While the embodiments described above have been presented as separate solutions for dealing with the problem of the relay node missing an ACK/NACK from the access node after sending an uplink transmission to the access node, it should be understood that these solutions could be combined in various combinations.

Other issues might arise when a relay node transmits to an access node at the same time that a UA is attempting to transmit to the relay node. In some cases, the relay node might be sending data on the uplink to the access node after receiving an uplink grant from the access node, and in other cases, the relay node might be sending an ACK/NACK on the uplink to the access node after receiving data on the downlink from the access node. In either case, if the UA attempts to transmit to the relay node in the same subframe in which the relay node is transmitting to the access node, the relay node will miss the transmission from the UA.

This can occur because, as mentioned above, the relay node can transmit control information to the UA in the first few symbols of what would otherwise be a reception subframe for the relay node. After transmitting the control information, the relay node can receive data from the access node in the remainder of the subframe. If the relay node provides an uplink grant to the UA, the UA will typically transmit to the relay node in a subframe that occurs 4 ms later. If the relay node receives data or an uplink grant from the access node, the relay node will send an ACK/NACK or data to the access node in a subframe that occurs 4 ms later. Therefore, if the relay node receives data or an uplink grant from the access node in the same subframe in which the relay node provided an uplink grant to the UA, the relay node will attempt to transmit to the access node in the same subframe in which the UA is attempting to transmit to the relay node. The relay node will miss the transmission from the UA when such a collision occurs.

In an embodiment, this situation can be addressed by the relay node sending the UA a "smart" NACK when the relay node knows that it has missed a transmission from the UA. The relay node knows that when it provides an uplink grant to the UA, the UA will transmit to the relay node 4 ms later. The relay node also knows that when it receives a transmission from the access node, the relay node will transmit to the access node 4 ms later. Therefore, the relay node knows that when it provides an uplink grant to the UA and receives a transmission from the access node in the same subframe, a collision will occur 4 ms later and the relay node will miss a transmission from the UA. In an embodiment, the relay node sends the UA a smart NACK message when the relay node knows that it has missed a transmission from the UA for this reason. The smart NACK message can be sent 4 ms or four subframes after the inferred collision. The UA can then retransmit the missed data packet to the relay node 4 ms or four subframes later. The NACK can be referred to as "smart" since it is based on the relay node being aware that a transmission from the UA has been missed due to a collision.

A data packet transmitted from the UA to the relay node typically uses a particular redundancy version. If the data packet needs to be retransmitted, the retransmission might use a redundancy version different from that used in the initial transmission. The two packets with the different redundancy versions might then be combined to increase the likelihood that the data will be properly decoded. When adaptive retransmission is used, the relay node explicitly signals the UA which redundancy version to use for a retransmission. When non-adaptive retransmission is used, the redundancy version to be used for a retransmission is determined by a periodic cycle of redundancy versions. For example, if a cycle of 0-2-1-3 is used, then redundancy version 0 would be used on the initial transmission, redundancy version 2 would be used on the first retransmission, redundancy version 1 would be used on the second retransmission, and redundancy version 3 would be used on the third retransmission. Redundancy version 0 typically includes more information and better information than the other redundancy versions for decoding purposes, so redundancy version 0 is typically used on an initial transmission. Additional information about redundancy versions can be found in 3rd Generation Partnership Project (3GPP) Technical Specification (TS) 36.212, which is incorporated herein by reference for all purposes.

When a data packet transmitted from the UA to the relay node is missed for the reason described above and is later retransmitted, it is known that the first data packet was never received and that it therefore cannot be combined with the retransmitted data packet. That is, the reason for the retransmission is not an inability of the relay node to decode the initial data packet, but the fact that the relay node never received the initial data packet at all.

In an embodiment, when the relay node misses a data packet for the reason described above and sends the UA a smart NACK, the UA retransmits the data packet using the same redundancy version that was used on the initial transmission. More specifically, since redundancy version 0 is typically used on an initial transmission and typically provides better performance, redundancy version 0 might be used when a UA retransmits a data packet after the UA receives a smart NACK. Alternatively, the UA could retransmit the data packet using the redundancy version that was used on the previous transmission. For example, if the UA transmits a data packet using redundancy version 0, but the relay node cannot decode the packet, the UA might then retransmit using redundancy version 2. If the relay node cannot receive the retransmitted packet (due to an uplink collision, for example), the UA would again retransmit with redundancy version 2. This would provide more diversity after being recombined with the data packet transmitted with redundancy version 0. Retransmitting with redundancy version 0 in such a case would provide no parity bit diversity for HARQ combining.

In an embodiment, when the relay node sends the UA a smart NACK, the relay node might include an indicator that informs the UA that the NACK is a smart NACK. Upon receiving the indicator, the UA knows to retransmit with an appropriate redundancy version. For example, the UA might be configured to retransmit with either the initial redundancy version, the previous redundancy version, or redundancy version 0 upon receiving the indicator. Alternatively, the indicator might explicitly instruct the UA to retransmit with either the initial redundancy version, the previous redundancy version, or redundancy version 0.

Figure 8:
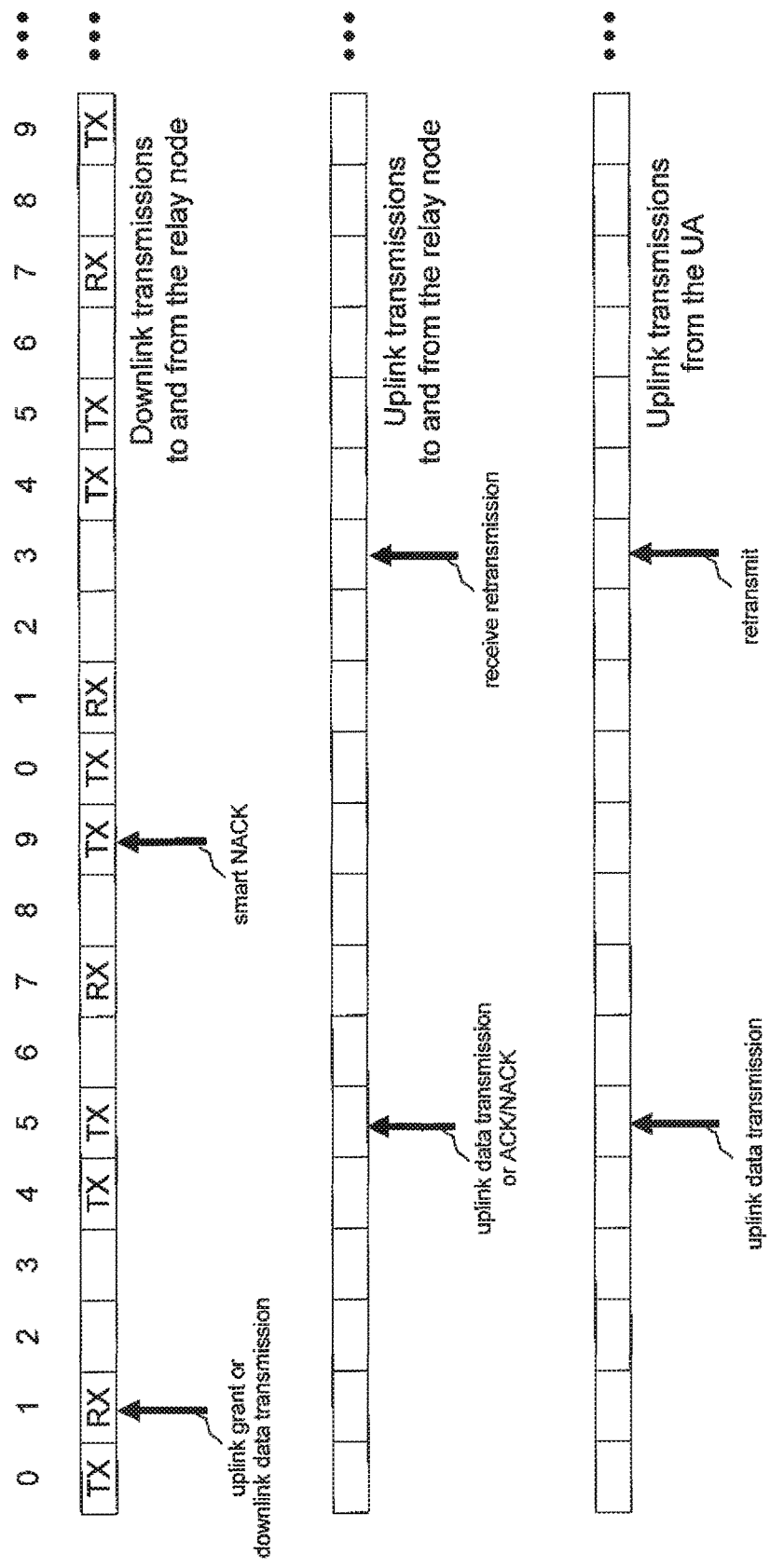
FIG. 8 is a diagram of multiple timelines depicting the use of a "smart" NACK according to an embodiment of the disclosure.

These embodiments are illustrated in FIG. 8. At subframe 1, a relay node receives a downlink transmission from an access node. In some cases, the downlink transmission might be an uplink grant from the access node, and in other cases, the downlink transmission might be a downlink data transmission from the access node. Also in subframe 1, the relay node provides an uplink grant to a UA. 4 ms later, at subframe 5, the UA attempts to transmit on the uplink to the relay node using the uplink grant that the relay node provided in subframe 1. Also in subframe 5, the relay node attempts to transmit on the uplink to the access node. In the cases where the downlink transmission from the access node to the relay node at subframe 1 was an uplink grant, the transmission from the relay node to the access node at subframe 5 is a data transmission. In the cases where the downlink transmission from the access node to the relay node at subframe 1 was a data transmission, the transmission from the relay node to the access node at subframe 5 is an ACK/NACK.

The relay node knows that, at subframe 5, the UA is attempting to transmit on the uplink to the relay node at the same time that the relay node is attempting to transmit on the uplink to the access node and that the transmission from the UA will be missed. Therefore, 4 ms after the transmission from the UA, at subframe 9, the relay node sends a smart NACK on the downlink to the UA informing the UA that the transmission at subframe 5 was missed. The NACK can be referred to as "smart" since it is based on the relay node being aware of the collision that occurred at subframe 5. 4 ms after receiving the smart NACK, at subframe 3 of the next radio frame, the UA retransmits the data that was previously transmitted at subframe 5, and the relay node receives the retransmission.

In an alternative embodiment, another technique is used to address the problem of the relay node missing a transmission from the UA when the UA attempts to transmit to the relay node in the same subframe in which the relay node is transmitting to the access node. In this technique, uplink transmissions from the relay node to the access node are fixed to occur at regular intervals, such as every 8 ms. Uplink transmissions from the UA to the relay node are then forbidden from occurring at those times. In this way, uplink transmissions from the relay node to the access node and uplink transmissions from the UA to the relay node never occur at the same time.

In order for the uplink transmissions from the relay node to the access node to occur at fixed times, modifications might be needed to the typical 4 ms interval between an uplink grant from the access node and an uplink transmission to the access node. In an embodiment, an uplink grant from the access node to the relay node occurs in an MBSFN subframe that is as short a time as possible ahead of a fixed uplink transmission from the relay node, but no less than 4 ms ahead of the fixed uplink transmission. For example, if a fixed uplink transmission is scheduled to occur in subframe 7, and if an MBSFN subframe occurs at subframe 3, the uplink grant for the fixed uplink transmission occurs in the MBSFN subframe at subframe 3. If a fixed uplink transmission is scheduled to occur in subframe 7, and if an MBSFN subframe does not occur at subframe 3 but does occur at subframe 2, the uplink grant for the fixed uplink transmission occurs in the MBSFN subframe at subframe 2, and so on. If a fixed uplink transmission is scheduled to occur in subframe 9, and if an MBSFN subframe occurs at subframe 6, 7, or 8, the uplink grant for the fixed uplink transmission does not occur in any of these MBSFN subframes, since these subframes are less than 4 ms ahead of the fixed uplink transmission.

Also, in order to ensure that uplink transmissions from the UA to the relay node are forbidden in the fixed subframes in which uplink transmissions from the relay node to the access node occur, modifications might be needed to the procedures by which the relay node sends data and uplink grants to the UA. More specifically, the relay node should not send data or an uplink grant to the UA 4 ms before a subframe in which the UA is forbidden from transmitting to the relay node, since sending data or an uplink grant to the UA in such a subframe will cause the UA to transmit an ACK/NACK or data to the relay node in the forbidden subframe. In addition, there may be some subframes in which the relay node would not transmit data to the UA since the subframes are MBSFN subframes, but in which the relay can provide an uplink grant to the UA since a subframe in which the UA is forbidden from transmitting to the relay node does not occur 4 ms later.

An example of this embodiment is illustrated in FIG. 9, where a timeline for downlink receptions by the relay node from the access node and downlink transmissions from the relay node to the UA is labeled R-DL, a timeline for uplink transmissions from the relay node to the access node is labeled R-UL, a timeline for downlink transmissions from the relay node to the UA is labeled A-DL, and a timeline for uplink transmissions from the UA to the relay node is labeled A-UL.

In this example, the relay node transmits on the uplink to the access node at regular 8 ms intervals labeled with the letter C in the R-UL timeline. To prevent collisions between these fixed relay node uplink transmissions, the UA is barred from transmitting to the relay node in these subframes. The subframes in which the UA is barred from transmitting are labeled with the letter G in the A-UL timeline. The UA's uplink HARQ process numbers associated with the subframes are also shown in the A-UL timeline. Since the UA cannot transmit in the "G" subframes, the uplink HARQ process in those subframes will not be available. In this example, since the "G" subframes are associated with HARQ process 0, HARQ process 0 will be lost. Since the "C" subframes, where the relay node transmits to the access node and where the UA is forbidden from transmitting to the relay node, occur at the same 8 ms interval as one cycle of HARQ processes, the same HARQ process will be lost out of every cycle of HARQ processes.

In order for the relay node to transmit on the uplink to the access node at the regularly spaced "C" subframes, the subframes in which the uplink grants are provided to the relay node for the uplink transmissions might need to be specified as described above. The uplink grants occur in MBSFN subframes, which are labeled with the letter B in the R-DL timeline. Subframes in which the relay node must transmit on the downlink to the UA are labeled with the letter A in the R-DL timeline.

In the example of FIG. 9, the "C" subframes occur at subframes 0, 8, 16, 24, and 32. For the "C" subframe that occurs at subframe 8, the relay node receives an uplink grant from the access node at subframe 3. The closest subframe to subframe 8 that is 4 or more ms ahead of subframe 8 is subframe 4. This is an "A" subframe in which downlink transmissions to the UA must be made, so subframe 4 cannot be an MBSFN subframe. The next closest subframe that is 4 ms or more ahead of subframe 8 is subframe 3. That subframe is not an "A" subframe, so that subframe is designated as an MBSFN subframe, and an uplink grant for the uplink transmission at subframe 8 is made in subframe 3.

For the "C" subframe that occurs at subframe 16, the relay node receives an uplink grant from the access node at subframe 12. Although subframe 13 is closer to subframe 16 and is not an "A" subframe in which downlink transmissions to the UA must be made, subframe 13 could not be used as an MBSFN subframe in this example since that subframe is less than 4 ms ahead of the "C" subframe at subframe 16.

For the "C" subframe that occurs at subframe 24, the relay node receives an uplink grant from the access node at subframe 18. The two closest subframes to subframe 24 that are 4 or more ms ahead of subframe 24 are subframes 19 and 20. Both of these are "A" subframes in which downlink transmissions to the UA must be made, so these cannot be MBSFN subframes. The next closest subframe that is 4 ms or more ahead of subframe 24 is subframe 18, so that subframe is designated as an MBSFN subframe, and an uplink grant for the uplink transmission at subframe 24 is made in subframe 18.

For the "C" subframe that occurs at subframe 32, the relay node receives an uplink grant from the access node at subframe 28 since that is the subframe that is as short a time as possible ahead of the "C" subframe, but is not less than 4 ms ahead of the "C" subframe and is not an "A" subframe.

Similarly, for the "C" subframe that occurs at subframe 0, the relay node receives an uplink grant from the access node at subframe 36 of the previous set of four radio frames, since that subframe is 4 ms ahead of the "C" subframe and is not an "A" subframe.

The "G" subframes in the A-UL timeline, where the UA is forbidden from transmitting to the relay node, are arranged to coincide with the "C" subframes in the R-UL timeline, where the relay node transmits to the access node. In order to ensure that no transmissions occur from the UA to the relay node in these "G" subframes, the downlink transmissions from the relay node to the UA, as shown in the A-DL timeline, may need to be arranged appropriately. A downlink data transmission from the relay node to the UA cannot occur in an MBSFN subframe since the relay node receives transmissions from the access node in MBSFN subframes, and the relay node cannot receive transmissions from the access node in the same subframe in which the relay node transmits data to the UA.

The subframes labeled D and F in the A-DL timeline coincide with MBSFN subframes, so data cannot be transmitted on the downlink from the relay node to the UA in the "D" and "F" subframes. The "F" subframes occur 4 ms before a "G" subframe in the A-UL timeline, so uplink grants should not be transmitted on the downlink from the relay node to the UA in the "F" subframes in order to prevent the UA from transmitting data on a granted uplink in a "G" subframe. That is, neither data nor uplink grants should be sent from the relay node to the UA in an "F" subframe. However, "D" subframes do not occur 4 ms before a "G" subframe, so uplink grants may be transmitted from the relay node to the UA in the "D" subframes since data that is transmitted on the granted uplink will not coincide with an uplink transmission from the relay node to the access node.

The "E" subframes in the A-DL timeline are subframes that are not MBSFN subframes but that occur 4 ms before a "G" subframe in the A-UL timeline. Neither data nor uplink grants should be sent from the relay node to the UA in an "E" subframe since a data transmission would cause an ACK/NACK to be sent in a "G" subframe, and an uplink grant would cause a data transmission to be sent in a "G" subframe.

In other embodiments, subframes other than 8, 16, 24, 32, and so on could be designated for relay node uplink transmissions to the access node, as long as the subframes maintain a regular 8 ms interval. In such a case, a different uplink HARQ process would be lost. For example, subframes 5, 13, 21, 29, and so on could be reserved for relay node transmissions to the access node, and UA transmissions to the relay node could be forbidden in those subframes. It can be seen from FIG. 9 that HARQ process 5 would be lost in such a case.

In an embodiment, a plurality of sets of subframes could be designated for relay node uplink transmissions to the access node, where a regular 8 ms interval is maintained between the subframes in each set. For example, subframes 8, 16, 24, 32, and so on could be reserved for relay node transmissions to the access node, and subframes 5, 13, 21, 29, and so on could also be reserved for relay node transmissions to the access node. UA transmissions to the relay node could be forbidden in all of those subframes. This embodiment would provide more opportunities for the relay node to transmit to the access node without collisions, but a plurality of HARQ processes would be lost out of every HARQ cycle. In this example, HARQ processes 0 and 5 would be unavailable.

The access node might send multiple transmissions of data on the downlink to the relay node before the next opportunity for the relay node to transmit corresponding ACK/NACKs for the data transmissions to the access node. The relay node might need to send the access node an ACK/NACK for each of the downlink transmissions, but it may not be efficient for the relay node to transmit the ACK/NACKs separately. In an embodiment, the relay node might aggregate the ACK/NACKs and send them to the relay node in a single subframe. The access node might need to inform the relay node how to perform the aggregation and, in alternative embodiments, there are two different ways in which the access node could do so.

In one embodiment, the access node explicitly tells the relay node which downlink transmissions to the relay node can have their ACK/NACKs aggregated and which subframe the relay node should use to send the aggregated ACK/NACK to the access node. For example, as shown in FIG. 10, the relay node might receive data from the access node in subframes 1, 2, and 3. The access node might explicitly or implicitly (for example, by some pre-defined rules) inform the relay node that the ACK/NACKs for the data transmitted in these subframes are to be aggregated together. The access node might also explicitly or implicitly (for example, by some pre-defined rules) inform the relay node of the subframe in which the aggregated ACK/NACK is to be returned to the access node. In this example, the access node has specified that the aggregated ACK/NACK is to be returned in subframe 7. In other examples, the access node might specify that the ACK/NACKs for data transmitted in other subframes should be aggregated and might specify another subframe as the subframe in which the aggregated ACK/NACK is to be returned. The access node might also explicitly or implicitly (for example, by some pre-defined rules) inform the relay node of the resources used to transmit the aggregated ACK/NACKs.

In an alternative embodiment, the access node includes a one-bit indicator with each downlink transmission to the relay node. The indicator indicates whether the ACK/NACK for that downlink transmission can be aggregated or should be transmitted the usual 4 ms after the downlink transmission. For example, one value for the indicator could indicate "do not transmit 4 ms later". That is, this value could indicate that the ACK/NACK for a downlink transmission in which the indicator is included should be held for aggregation with later ACK/NACKs. Another value for the indicator could indicate "transmit 4 ms later". That is, this value could indicate that the ACK/NACK for a downlink transmission in which the indicator is included and any other previous ACK/NACKs that have been aggregated should be transmitted 4 ms after the downlink transmission is received.

In this embodiment, if the relay node misses an indicator, the aggregated ACK/NACKs could lose their synchronization. For example, if a "transmit 4 ms later" indicator is missed, the relay will wait for the next "transmit 4 ms later" indicator to transmit ACK/NACKs, but the access node will try to decode what it assumes are ACK/NACKs that should have been sent after the first "transmit 4 ms later" indicator. To remedy this situation, if the access node can detect that its attempts at decoding ACK/NACKs are out of synchronization with the relay node's transmissions of ACK/NACKs, the access node can recover by sending multiple "transmit 4 ms later" indicators. Alternatively, this situation might be avoided if the eNB periodically sends "transmit 4 ms later" indicators.

In either technique by which the access node informs the relay node about how to perform aggregation, aggregated ACK/NACKs can be transmitted in the same subframe as regular uplink data. In cases where Multiple Input Multiple Output (MIMO) is used, each transmission can consist of two code words, and the multiplexing of the aggregated ACK/NACKs with the code words of regular data can be done in several different ways. For example, a first ACK/NACK for subframe 1 could be multiplexed with code word 1 of a regular data transmission from the relay node to the access node, and then a second ACK/NACK for subframe 1 could be multiplexed with code word 2. This pattern could then be repeated for the ACK/NACKs for subframes 2 and 3. In another example, a first ACK/NACK for subframe 1, a first ACK/NACK for subframe 2, and a first ACK/NACK for subframe 3 could be multiplexed with code word 1 of a regular data transmission. This pattern could then be repeated for code word 2. Other multiplexing methods may be apparent to one of skill in the art.

Figure 11:
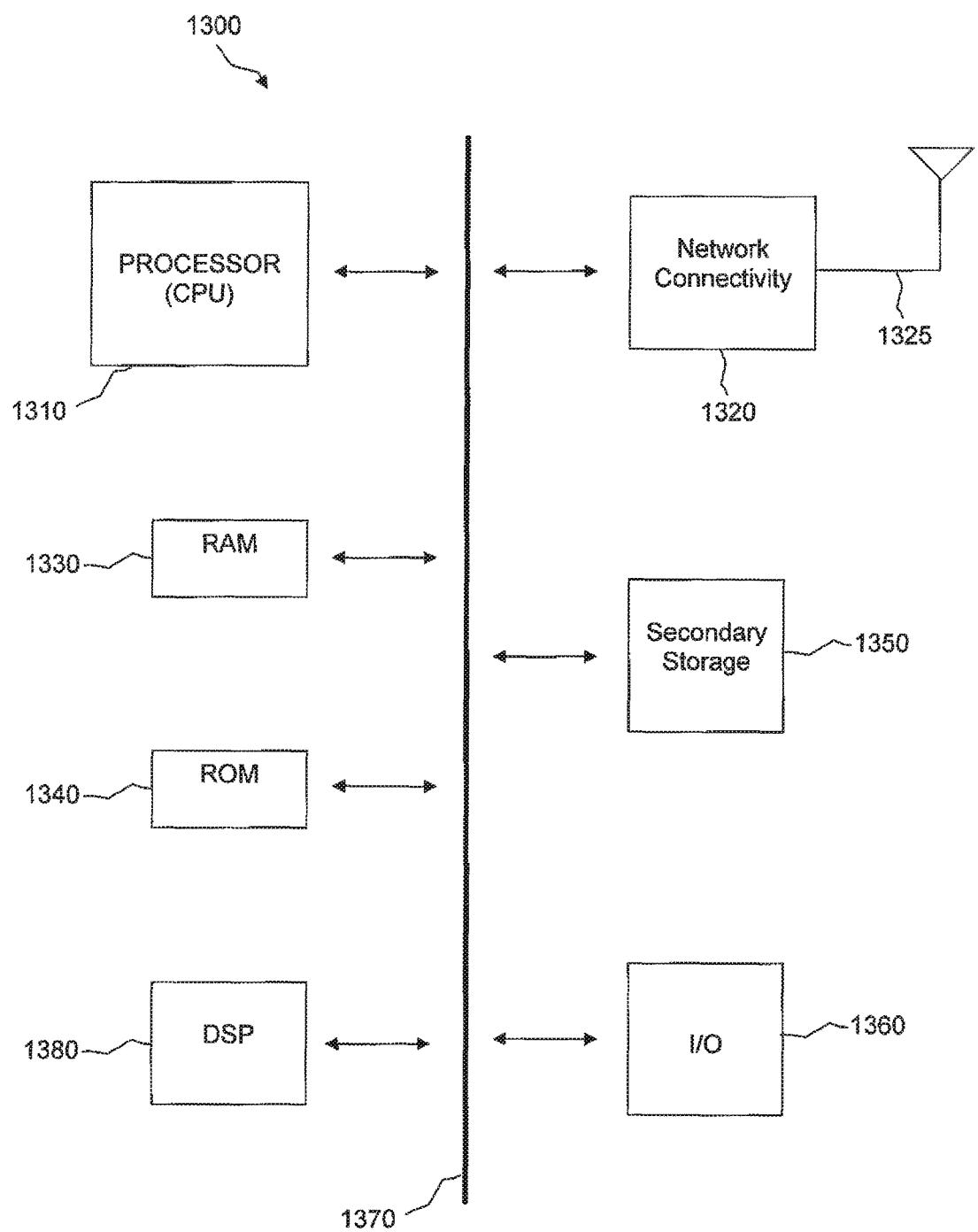
FIG. 11 illustrates a processor and related components suitable for implementing the several embodiments of the present disclosure.

The UA 110, the relay node 102, the access node 106, and other components described above might include a processing component that is capable of executing instructions related to the actions described above. FIG. 11 illustrates an example of a system 1300 that includes a processing component 1310 suitable for implementing one or more embodiments disclosed herein. In addition to the processor 1310 (which may be referred to as a central processor unit or CPU), the system 1300 might include network connectivity devices 1320, random access memory (RAM) 1330, read only memory (ROM) 1340, secondary storage 1350, and input/output (I/O) devices 1360. These components might communicate with one another via a bus 1370. In some cases, some of these components may not be present or may be combined in various combinations with one another or with other components not shown. These components might be located in a single physical entity or in more than one physical entity. Any actions described herein as being taken by the processor 1310 might be taken by the processor 1310 alone or by the processor 1310 in conjunction with one or more components shown or not shown in the drawing, such as a digital signal processor (DSP) 1380. Although the DSP 1380 is shown as a separate component, the DSP 1380 might be incorporated into the processor 1310.

The processor 1310 executes instructions, codes, computer programs, or scripts that it might access from the network connectivity devices 1320, RAM 1330, ROM 1340, or secondary storage 1350 (which might include various disk-based systems such as hard disk, floppy disk, or optical disk). While only one CPU 1310 is shown, multiple processors may be present. Thus, while instructions may be discussed as being executed by a processor, the instructions may be executed simultaneously, serially, or otherwise by one or multiple processors. The processor 1310 may be implemented as one or more CPU chips.

The network connectivity devices 1320 may take the form of modems, modem banks, Ethernet devices, universal serial bus (USB) interface devices, serial interfaces, token ring devices, fiber distributed data interface (FDDI) devices, wireless local area network (WLAN) devices, radio transceiver devices such as code division multiple access (CDMA) devices, global system for mobile communications (GSM) radio transceiver devices, worldwide interoperability for microwave access (WiMAX) devices, and/or other well-known devices for connecting to networks. These network connectivity devices 1320 may enable the processor 1310 to communicate with the Internet or one or more telecommunications networks or other networks from which the processor 1310 might receive information or to which the processor 1310 might output information. The network connectivity devices 1320 might also include one or more transceiver components 1325 capable of transmitting and/or receiving data wirelessly.

The RAM 1330 might be used to store volatile data and perhaps to store instructions that are executed by the processor 1310. The ROM 1340 is a non-volatile memory device that typically has a smaller memory capacity than the memory capacity of the secondary storage 1350. ROM 1340 might be used to store instructions and perhaps data that are read during execution of the instructions. Access to both RAM 1330 and ROM 1340 is typically faster than to secondary storage 1350. The secondary storage 1350 is typically comprised of one or more disk drives or tape drives and might be used for non-volatile storage of data or as an over-flow data storage device if RAM 1330 is not large enough to hold all working data. Secondary storage 1350 may be used to store programs that are loaded into RAM 1330 when such programs are selected for execution.

The I/O devices 1360 may include liquid crystal displays (LCDs), touch screen displays, keyboards, keypads, switches, dials, mice, track balls, voice recognizers, card readers, paper tape readers, printers, video monitors, or other well-known input/output devices. Also, the transceiver 1325 might be considered to be a component of the I/O devices 1360 instead of or in addition to being a component of the network connectivity devices 1320.

In an embodiment, a method is provided for preventing a relay node from missing a transmission from an access node. The method includes, when a ten millisecond periodicity is used for Multicast/Broadcast Single Frequency Network (MBSFN) subframes, setting a time between an uplink grant from the access node to the relay node and an acknowledgement/negative-acknowledgement message (ACK/NACK)

from the access node to the relay node equal to ten milliseconds. The method further includes, when a forty millisecond periodicity is used for MBSFN subframes, the access node sending the relay node an asynchronous grant for an uplink retransmission when a data packet is missed, and when the relay node receives the grant for the uplink retransmission, the relay node retransmitting the missed data packet.

In another embodiment, an access node in a wireless telecommunications system is provided. The access node includes a processor configured, when a ten millisecond periodicity is used for Multicast/Broadcast Single Frequency Network (MBSFN) subframes, to set a time between an uplink grant from the access node to a relay node and an acknowledgement/negative-acknowledgement message (ACK/NACK) from the access node to the relay node equal to ten milliseconds. The processor is further configured, when a forty millisecond periodicity is used for MBSFN subframes, to send the relay node a grant for an uplink retransmission when a data packet is missed.

In another embodiment, a relay node in a wireless telecommunications system is provided. The relay node includes a processor configured, when a ten millisecond periodicity is used for Multicast/Broadcast Single Frequency Network (MBSFN) subframes, to receive an acknowledgement/negative-acknowledgement message (ACK/NACK) from an access node. The time between an uplink grant from the access node to the relay node and the ACK/NACK from the access node to the relay node is set equal to ten milliseconds. The processor is further configured, when a forty millisecond periodicity is used for MBSFN subframes, to receive from the access node an asynchronous grant for an uplink retransmission when a data packet is missed. The processor is further configured to retransmit the missed data packet when the relay node receives the grant for the uplink retransmission.

In another embodiment, a method is provided for preventing a relay node from missing a transmission from an access node. The method includes the access node sending an acknowledgement/negative-acknowledgement message (ACK/NACK) to the relay node in the first available Multicast/Broadcast Single Frequency Network (MBSFN) subframe that is at least four milliseconds after an uplink transmission from the relay node.

In another embodiment, an access node in a wireless telecommunications system is provided. The access node includes a processor configured to send an acknowledgement/negative-acknowledgement message (ACK/NACK) to a relay node in the first available Multicast/Broadcast Single Frequency Network (MBSFN) subframe that is at least four milliseconds after an uplink transmission from the relay node.

In another embodiment, a relay node in a wireless telecommunications system is provided. The relay node includes a processor configured to receive an acknowledgement/negative-acknowledgement message (ACK/NACK) from an access node in the first available Multicast/Broadcast Single Frequency Network (MBSFN) subframe that is at least four milliseconds after an uplink transmission from the relay node.

In another embodiment, a method is provided for preventing a relay node from missing a transmission from an access node. The method includes, for every Multicast/Broadcast Single Frequency Network (MBSFN) subframe in which the access node grants an uplink resource to the relay node, assigning a corresponding MBSFN subframe in which the access node can transmit an acknowledgement/negative-acknowledgement message (ACK/NACK) to the relay node for an uplink transmission that the relay node sent to the access node on the granted resource.

In another embodiment, an access node in a wireless telecommunications system is provided. The access node includes a processor configured to transmit an acknowledgement/negative-acknowledgement message (ACK/NACK) to a relay node for an uplink transmission that the relay node sent to the access node, wherein, for every Multicast/Broadcast Single Frequency Network (MBSFN) subframe in which the access node grants an uplink resource to the relay node, a corresponding MBSFN subframe has been assigned in which the access node can transmit the ACK/NACK.

In another embodiment, a relay node in a wireless telecommunications system is provided. The relay node includes a processor configured to receive an acknowledgement/negative-acknowledgement message (ACK/NACK) from an access node for an uplink transmission that the relay node sent to the access node, wherein, for every Multicast/Broadcast Single Frequency Network (MBSFN) subframe in which the access node grants an uplink resource to the relay node, a corresponding MBSFN subframe has been assigned in which the access node can transmit the ACK/NACK.

In another embodiment, a method is provided for preventing a relay node from missing a transmission from a user agent (UA). The method includes, when the UA transmits a data packet to the relay node in the same subframe in which the relay node is transmitting to an access node, the relay node sending the UA a negative-acknowledgement message (NACK).

In another embodiment, a relay node in a wireless telecommunications system is provided. The relay node includes a processor configured to send a negative-acknowledgement message (NACK) to a user agent (UA) when the UA transmits a data packet to the relay node in the same subframe in which the relay node is transmitting to an access node.

In another embodiment, a user agent (UA) is provided. The UA includes a processor configured to receive a negative-acknowledgement message (NACK) from a relay node when the UA transmits a data packet to the relay node in the same subframe in which the relay node is transmitting to an access node.

In another embodiment, a method is provided for preventing a relay node from missing a transmission from a user agent (UA). The method includes transmitting from the relay node to an access node only at fixed intervals. The method further includes forbidding transmissions from the UA to the relay node during subframes in which the fixed transmissions from the relay node to the access node occur.

In another embodiment, a relay node in a wireless telecommunications system is provided. The relay node includes a processor configured to transmit to an access node only at fixed intervals, wherein transmissions from a user agent (UA) to the relay node are forbidden during subframes in which the fixed transmissions from the relay node to the access node occur.

In another embodiment, an access node in a wireless telecommunications system is provided. The access node includes a processor configured to receive transmissions from a relay node, wherein the transmissions occur only at fixed intervals, and wherein transmissions from a user agent (UA) to the relay node are forbidden during subframes in which the fixed transmissions from the relay node to the access node occur.

In another embodiment, a method is provided for managing a plurality of acknowledgement/negative-acknowledgement messages (ACK/NACKs). The method includes, when an access node sends multiple transmissions of data to a relay node before the next opportunity for the relay node to transmit corresponding ACK/NACKs for the data transmissions to the access node, the relay node aggregating the ACK/NACKs and sending the aggregated ACK/NACKs to the access node in a single subframe.

In another embodiment, a relay node in a wireless telecommunications system is provided. The relay node includes a processor configured to aggregate a plurality of acknowledgement/negative-acknowledgement messages (ACK/NACKs) when an access node sends multiple transmissions of data to the relay node before the next opportunity for the relay node to transmit corresponding ACK/NACKs for the data transmissions to the access node. The processor is further configured to send the aggregated ACK/NACKs to the access node in a single subframe.

In another embodiment, an access node in a wireless telecommunications system is provided. The access node includes a processor configured to receive an aggregated acknowledgement/negative-acknowledgement message (ACK/NACK) in a single subframe from a relay node, the aggregated ACK/NACK being formed from a plurality of ACK/NACKs when the access node sends multiple transmissions of data to the relay node before the next opportunity for the relay node to transmit corresponding ACK/NACKs for the data transmissions to the access node.

The following is incorporated herein by reference for all purposes: 3rd Generation Partnership Project (3GPP) Technical Specification (TS) 36.212. Appendices A and B which are attached hereto are also incorporated by reference.

While several embodiments have been provided in the present disclosure, it should be understood that the disclosed systems and methods may be embodied in many other specific forms without departing from the scope of the present disclosure. The present examples are to be considered as illustrative and not restrictive, and the intention is not to be limited to the details given herein. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A relay node in a wireless telecommunications system, comprising:
    a processor configured to determine whether a collision will occur in a future subframe, wherein the collision results in a transmission from a user agent (UA) being missed by the relay node;
    a transmitter coupled to the processor and configured to provide an uplink grant to the UA in a first subframe; and
    a receiver coupled to the processor and configured to receive a transmission from an access node (AN) in the first subframe,
    wherein, when the processor determines that the collision will occur, the transmitter is further configured to send a smart negative-acknowledgement message (smart NACK) to the UA indicating that the transmission from the UA is missed by the relay node due to the collision, wherein the smart NACK comprises an indicator comprising one or more bits to indicate that the smart NACK is the smart NACK rather than a regular NACK, and
    wherein the collision comprises a collision between the relay node transmitting to the AN in the future subframe in which the UA is to transmit data to the relay node in response to the uplink grant such that the transmission from the UA to the relay node is missed.

2. The relay node of claim 1, wherein the relay node sends the smart NACK eight subframes after the first subframe in which the relay node provided the uplink grant to the UA and in which the relay node received the transmission from the AN.

3. The relay node of claim 1, wherein the indicator informs the UA that the smart NACK was sent because the relay node did not receive the transmission from the UA, wherein the regular NACK would otherwise have been sent if the relay node was unable to decode the transmission from the UA.

4. The relay node of claim 3, wherein the receiver is further configured to receive a retransmission of a data packet subsequent to transmitting the smart NACK including the indicator, wherein the data packet comprises a redundancy version with which the data packet was initially transmitted during the transmission from the UA to the relay node at the future subframe.

5. The relay node of claim 3, wherein the indicator further informs the UA to retransmit a data packet using a same redundancy version as that used when the data packet was previously transmitted during the transmission from the UA to the relay node at the future subframe.

6. The relay node of claim 3, wherein the receiver is further configured to receive a retransmission of a data packet subsequent to transmitting the smart NACK including the indicator, the data packet corresponding to the missed transmission at the future subframe, and wherein the retransmitted data packet comprises a redundancy version 0 if the data packet corresponding to the missed transmission was an initial transmission of the data packet.

7. A user agent (UA), comprising:
    a receiver coupled to a processor and configured to receive a smart negative-acknowledgement message (smart NACK) from a relay node when the UA transmits a data packet to the relay node in a same subframe in which the relay node is transmitting to an access node (AN),
    wherein the smart NACK comprises an indication that a transmission of the data packet from the UA is missed by the relay node due to a collision in the same subframe,
    wherein the relay node is configured to provide an uplink grant to the UA and receive a transmission from the AN in a first subframe, and
    wherein the collision comprises a collision between the relay node transmitting to the AN and the transmission of the data packet from the UA to the relay node in response to the uplink grant such that the transmission from the UA to the relay node is missed; and a transmitter coupled to the processor and configured to retransmit the data packet using a redundancy version, wherein the redundancy version is based on an indicator included in the smart NACK, wherein the indicator comprising one or more bits to indicate that the smart NACK is the smart NACK rather than a regular NACK.

8. The UA of claim 7, wherein the UA receives the smart NACK eight subframes after the first subframe in which the relay node provided the uplink grant to the UA and in which the relay node received the transmission from the AN.

9. The UA of claim 7, wherein the redundancy version 0 is used on the retransmission of the data packet if the missed transmission of the data packet was an initial transmission of the data packet.

10. The UA of claim 7, wherein the indicator informs the UA to retransmit the data packet using a same redundancy version with which the data packet was initially transmitted.

11. The UA of claim 7, wherein the indicator informs the UA that the smart NACK was sent because the relay node never received the data packet, wherein the UA would otherwise have received the regular NACK if the relay node was unable to decode the data packet.

12. The UA of claim 7, wherein the indicator informs the UA to retransmit the data packet using a different redundancy version than a redundancy version with which the data packet was previously transmitted.

13. The UA of claim 7, wherein the indicator informs the UA to retransmit the data packet using a redundancy version 0.

14. A method implemented by a network node, comprising:
   determining whether a collision will occur in a future subframe, wherein the collision results in a transmission of a data packet being missed by the network node;
   providing an uplink grant to a user agent (UA) in a first subframe preceding the collision;
   receiving a transmission from an access node (AN) in the first subframe; and
   transmitting a smart negative-acknowledgement message (smart NACK) to the UA in response to determining that the transmission from the UA is missed by the network node due to the collision, the smart NACK indicating that the transmission from the UA was missed, wherein the smart NACK includes an indicator comprising one or more bits to indicate that the smart NACK is the a smart NACK rather than a regular NACK, and wherein the collision comprises a collision between the network node transmitting to the AN in the future subframe in which the UA is to transmit data to the network node in response to the uplink grant such that the transmission from the UA to the network node is missed.

15. The method of claim 14, wherein the network node sends the smart NACK eight subframes after the first subframe in which the network node provided the uplink grant to the UA and in which the network node received a transmission from the AN.

16. The method of claim 14, wherein the indicator informs the UA that the smart NACK was sent because the network node never received the data packet from the UA, wherein the regular NACK would otherwise have been sent if the network node was unable to decode the data packet from the UA.

17. The method of claim 16, further comprising receiving the data packet subsequent to transmitting the smart NACK including the indicator, wherein the data packet comprises a redundancy version with which the data packet was initially transmitted.

18. The method of claim 16, further comprising receiving a retransmission of a data packet subsequent to transmitting the smart NACK including the indicator, wherein the data packet comprises a redundancy version with which the data packet was previously transmitted.

19. The method of claim 16, further comprising receiving a retransmission of a data packet subsequent to transmitting the smart NACK including the indicator, wherein the data packet comprises a redundancy version 0.

20. The method of claim 14, wherein the network node is at least one of a relay node, an access node, an E-node B, a wireless access point, a layer one relay node, a layer two relay node, a layer 3 relay node, a pico-cell, and a femto-cell.

* * * * *